United States Patent
Parks

(10) Patent No.: US 6,948,813 B2
(45) Date of Patent: Sep. 27, 2005

(54) LENS ASSEMBLY PARTS AND ASSEMBLIES THEREFROM

(75) Inventor: Gerald R. Parks, Chula Vista, CA (US)

(73) Assignee: Dye Precision, Inc., San Diego, CA (US)

( * ) Notice: Subject to any disclaimer, the term of this patent is extended or adjusted under 35 U.S.C. 154(b) by 133 days.

(21) Appl. No.: 10/349,274

(22) Filed: Jan. 21, 2003

(65) Prior Publication Data

US 2004/0139532 A1 Jul. 22, 2004

(51) Int. Cl.$^7$ .................................................. G02C 1/00
(52) U.S. Cl. ..................... 351/158; 351/62; 351/154; 2/436
(58) Field of Search .......................... 351/41, 158, 140, 351/141, 44, 62, 83, 86, 154; 2/9, 12, 15, 426–437, 442, 443, 452, 453

(56) References Cited

U.S. PATENT DOCUMENTS

| | | | |
|---|---|---|---|
| 4,101,983 A | 7/1978 | Dera et al. | |
| 4,768,231 A * | 9/1988 | Schrack | 2/13 |
| D317,063 S | 5/1991 | Johnson | |
| D344,160 S | 2/1994 | Boza | |
| 5,617,588 A | 4/1997 | Canavan et al. | |
| 5,682,621 A * | 11/1997 | Park | 2/441 |
| 6,332,682 B1 * | 12/2001 | Yoshida | 351/153 |
| 6,363,528 B1 | 4/2002 | Cyr | |
| 6,370,695 B2 | 4/2002 | Paris et al. | |
| 6,381,749 B1 | 5/2002 | Cyr | |
| 2003/0140403 A1 * | 7/2003 | Chou | 2/428 |
| 2004/0060101 A1 * | 4/2004 | Shiue | 2/426 |

* cited by examiner

Primary Examiner—Huy Mai
(74) Attorney, Agent, or Firm—Richard D. Clarke

(57) ABSTRACT

A set of lens assembly parts which contains a base and a frame and at least one or more of a lens, fasteners for securing the lens between the base and the frame, a mask, and a strap. Lens assemblies formed from the set of lens assembly parts.

21 Claims, 16 Drawing Sheets

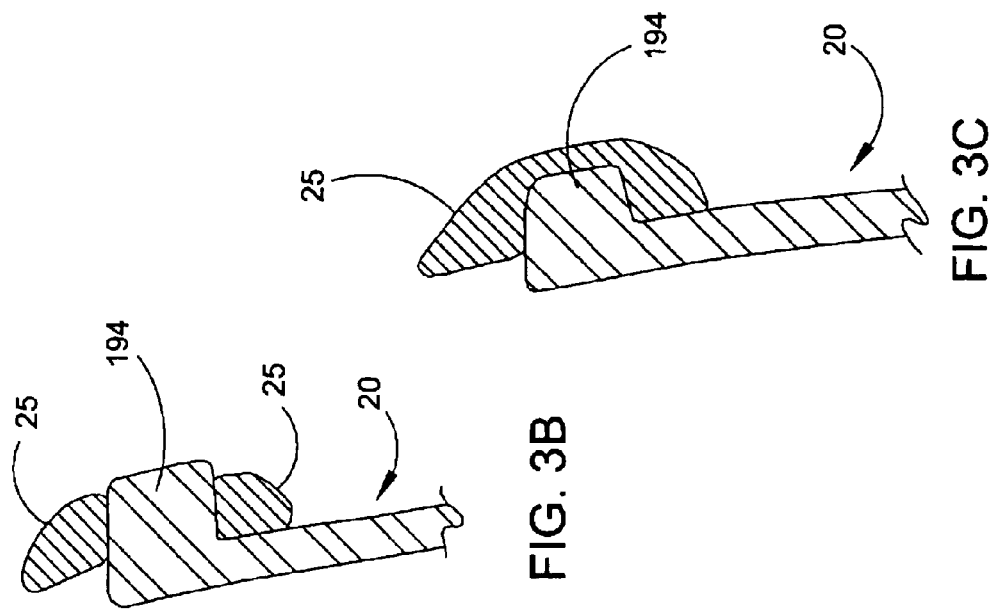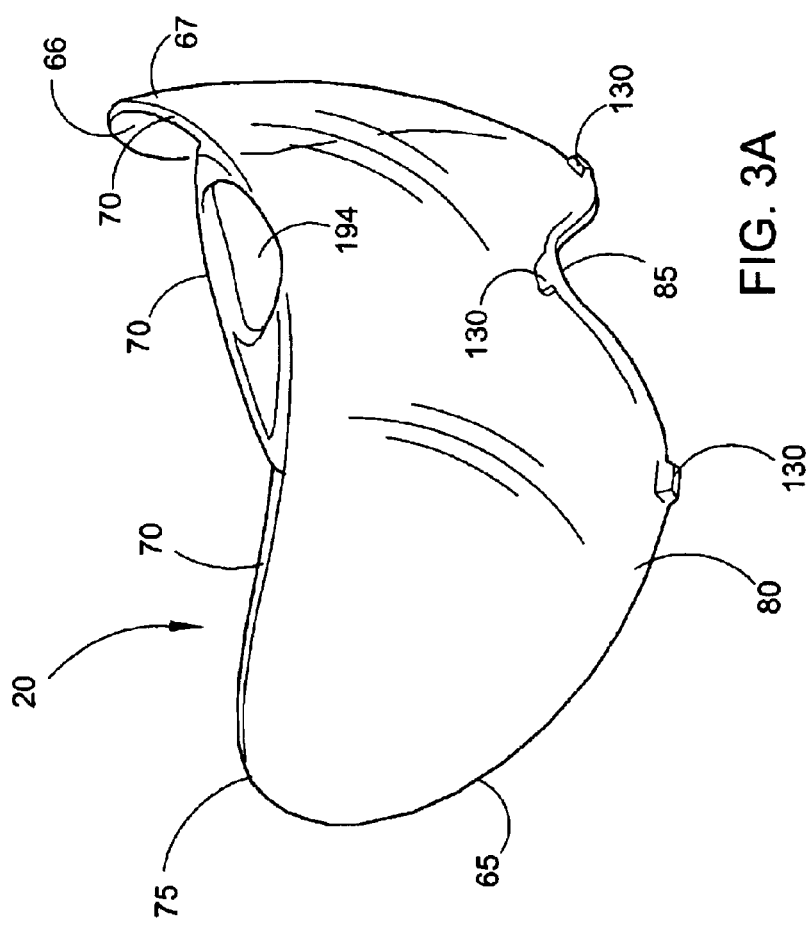

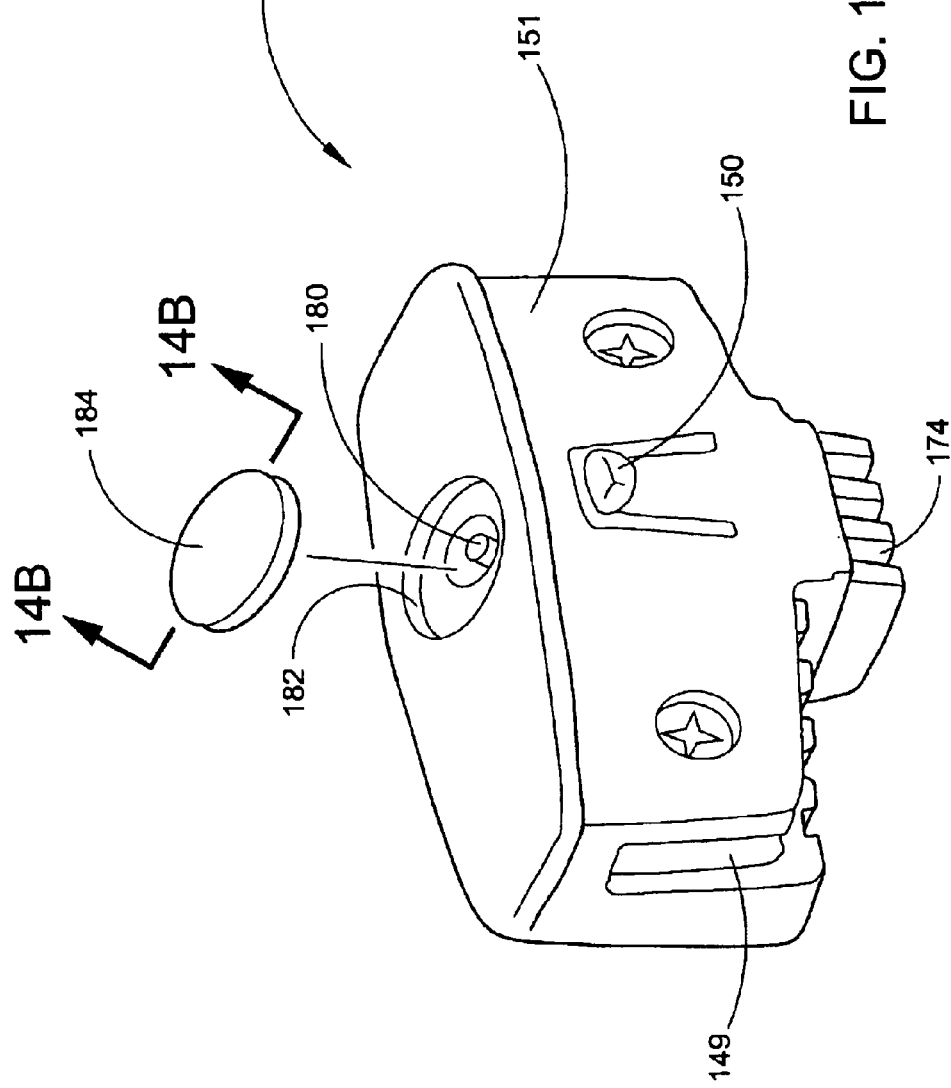

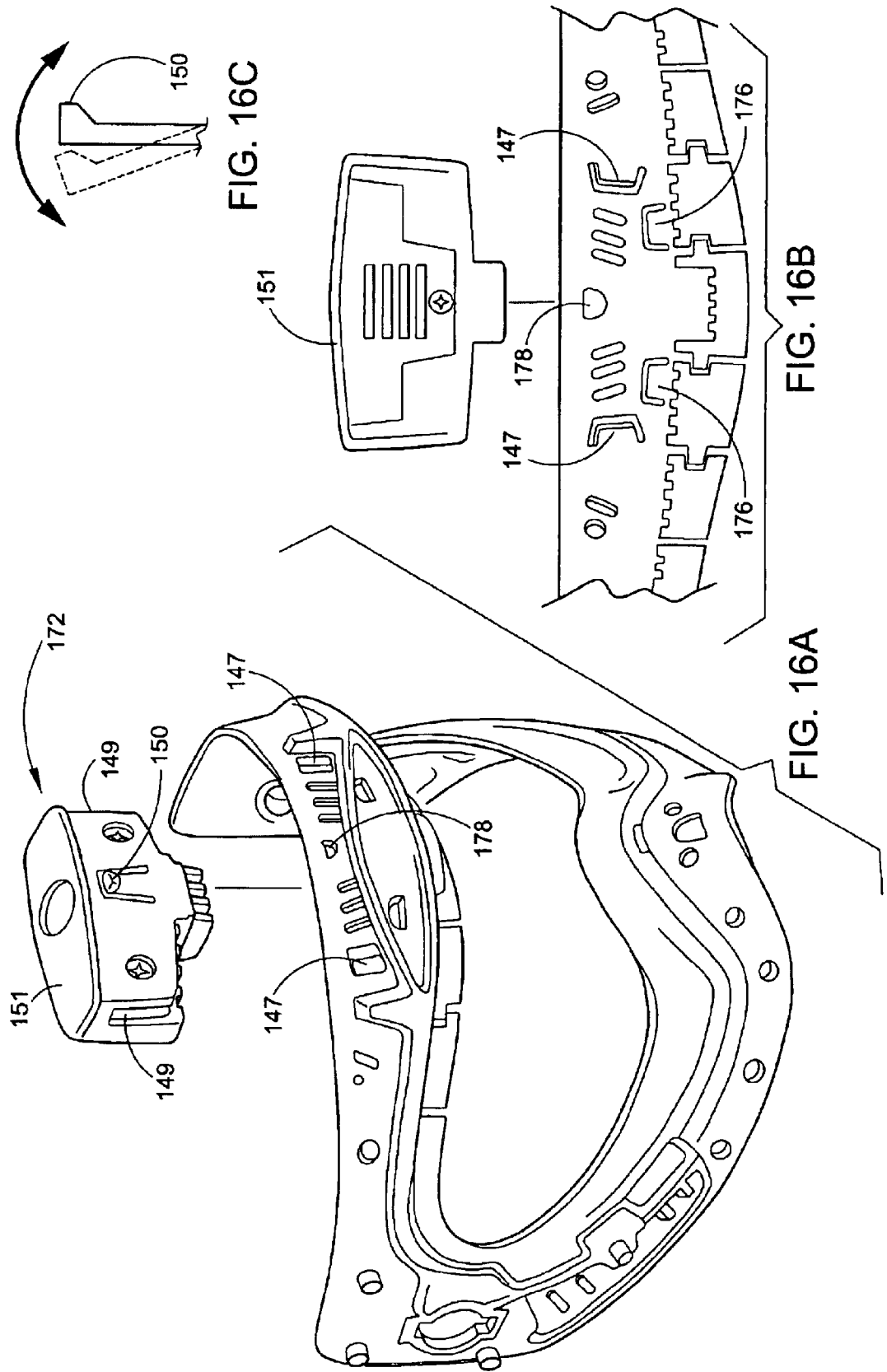

US 6,948,813 B2

LENS ASSEMBLY PARTS AND ASSEMBLIES THEREFROM

FIELD OF THE INVENTION

The present invention relates to a set of lens-assembly parts for a protective goggle and to lens assemblies formed therefrom.

BACKGROUND OF THE INVENTION

Eye protection in sports, industry, military and police activities typically involves use of a goggle or lens assembly, often in association with a face mask in order to fully cover the face and the sides of the user's head. To prevent eye injury from impact by projectiles, splashed or projected liquids, and other flying objects, the lens is securely mounted in such assemblies to prevent dislodgement or disengagement from the assembly. Goggles or goggle-mask systems combinations are difficult to disassemble for changing lenses or for cleaning. The present invention addresses this problem, and provides a set of lens assembly parts and of assemblies therefrom for easy assembly/disassembly for replacing and/or cleaning the lens, for the replacement of other portions of the assembly, and for cleaning the assembly.

SUMMARY OF THE INVENTION

The invention is directed to sets of lens assembly parts and lens assemblies formed from the sets. In one aspect, a set of lens assembly parts comprises a base which is shaped to fit over the eyes and which has a lens receiving portion and a frame shaped for registration with the base. The base as well as the frame each comprise opposite temple portions. A lens, which is shaped to be positioned and secured between the base and the frame, may be included in the set. The opposite temple portions of the frame and the base comprise fasteners for tensioning the base against the frame and for securing the lens. The fasteners are inserted in registration openings which are formed in the frame and the base, and in which openings protrusion-retention elements (e.g. twist locks) are positioned. A version of the set of assembly parts contains a mask, which after assembly, is attached to the base. The set may contain a strap sized for fitting a lens assembly, which is made from the set of parts, to the head of the user.

Subjects of the invention further include lens assemblies formed from various combinations of lens-assembly parts.

BRIEF DESCRIPTION OF DRAWINGS

FIG. 3 is a perspective view of a lens, and FIG. 3B–3C illustrate alternative placements of a logo tab of the lens in a corresponding slot.

FIGS. 14A–14B show a fan housing which is included in one set of lens assembly parts, and a cross-section of the logo disk housed in the fan housing.

FIG. 16A discloses an exploded view of the base and fan housing; FIG. 16B shows an exploded view of the fan and the fan retention tabs on the mask; and FIG. 16C shows the flexing movement of the fan retention clip.

DESCRIPTION OF THE DRAWINGS AND THE INVENTION

In one aspect, the subject invention involves a set of parts for forming a lens-assembly. Included in the invention are different lens-assemblies formed from the set of parts.

Figure 1:
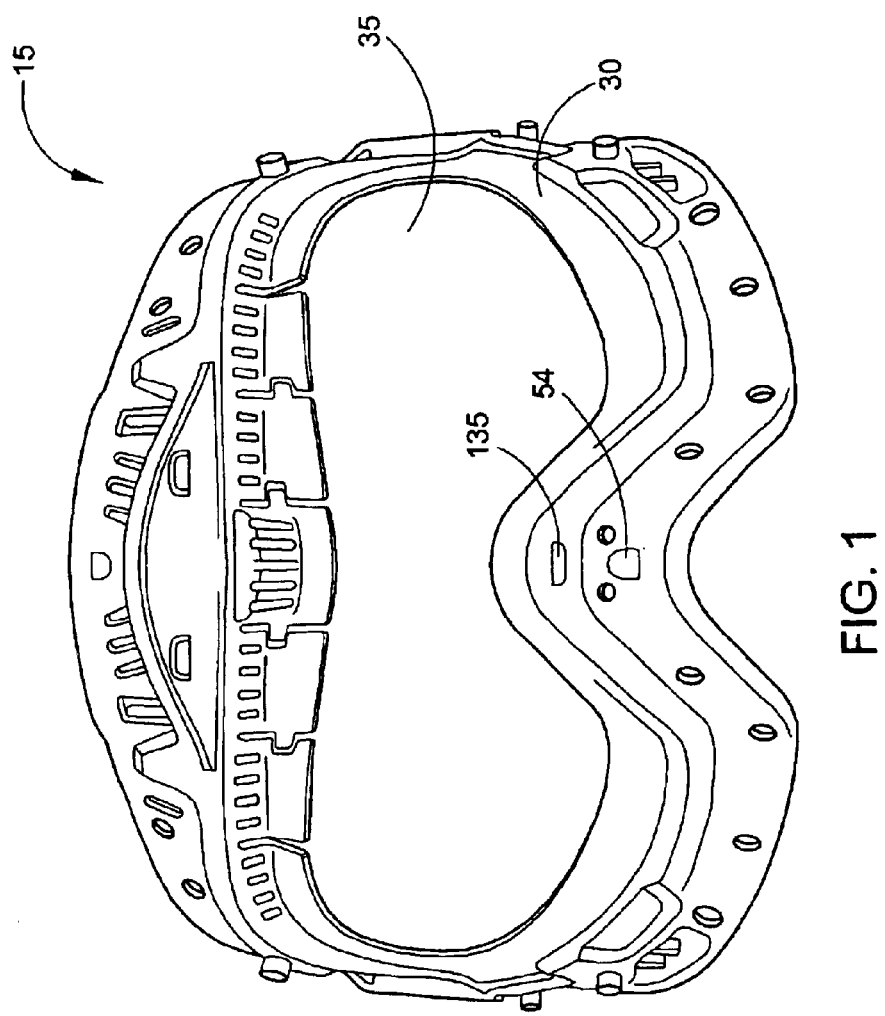
FIG. 1 is a front view of a base.
Figure 2:
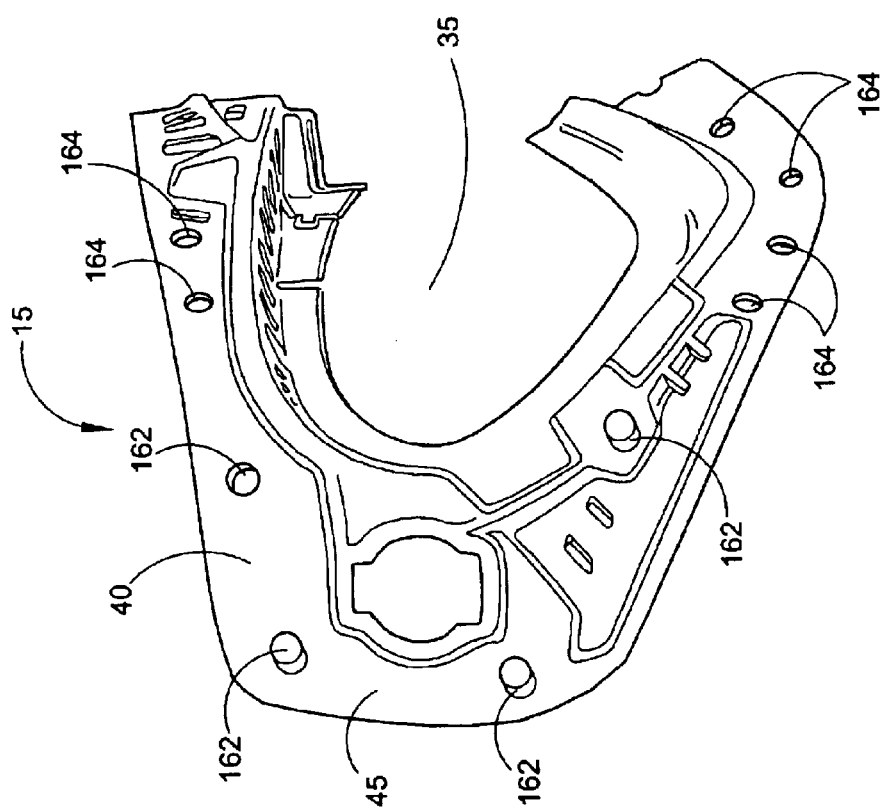
FIG. 2 is a side view of the base of FIG. 1.

The set of lens-assembly parts of the invention involves a base 15 which is formed of rigid or flexible plastic (FIGS. 1 and 2). The base is shaped to fit over the eyes. Formed in the base is a lens receiving portion 30 which is configured for receiving a lens 20 (FIG. 3). This lens receiving portion 30 defines a lens opening 35. Opposite temple portions 40 of the base extend rearward from the lens opening, and terminate in base terminal sections 45. A frame 25 (FIG. 4), also formed from rigid or flexible plastic material, is configured for mating alignment or engagement with the lens 20 to be positioned in the lens receiving portion 30 of the base. An opening 50 in the frame 25 registers with the lens opening 35 in the base 15. Opposite temple portions 55 of the frame extend rearward from the frame opening and terminate in frame terminal sections 60. In the lens assembly 10 (FIG. 5) formed therefrom, the opposite temple portions of the base and frame, respectively 40 and 55, are configured to be in juxtaposition in a lens assembly formed therefrom, forming opposite terminal regions 62 of the lens assembly of the invention.

Figure 6:
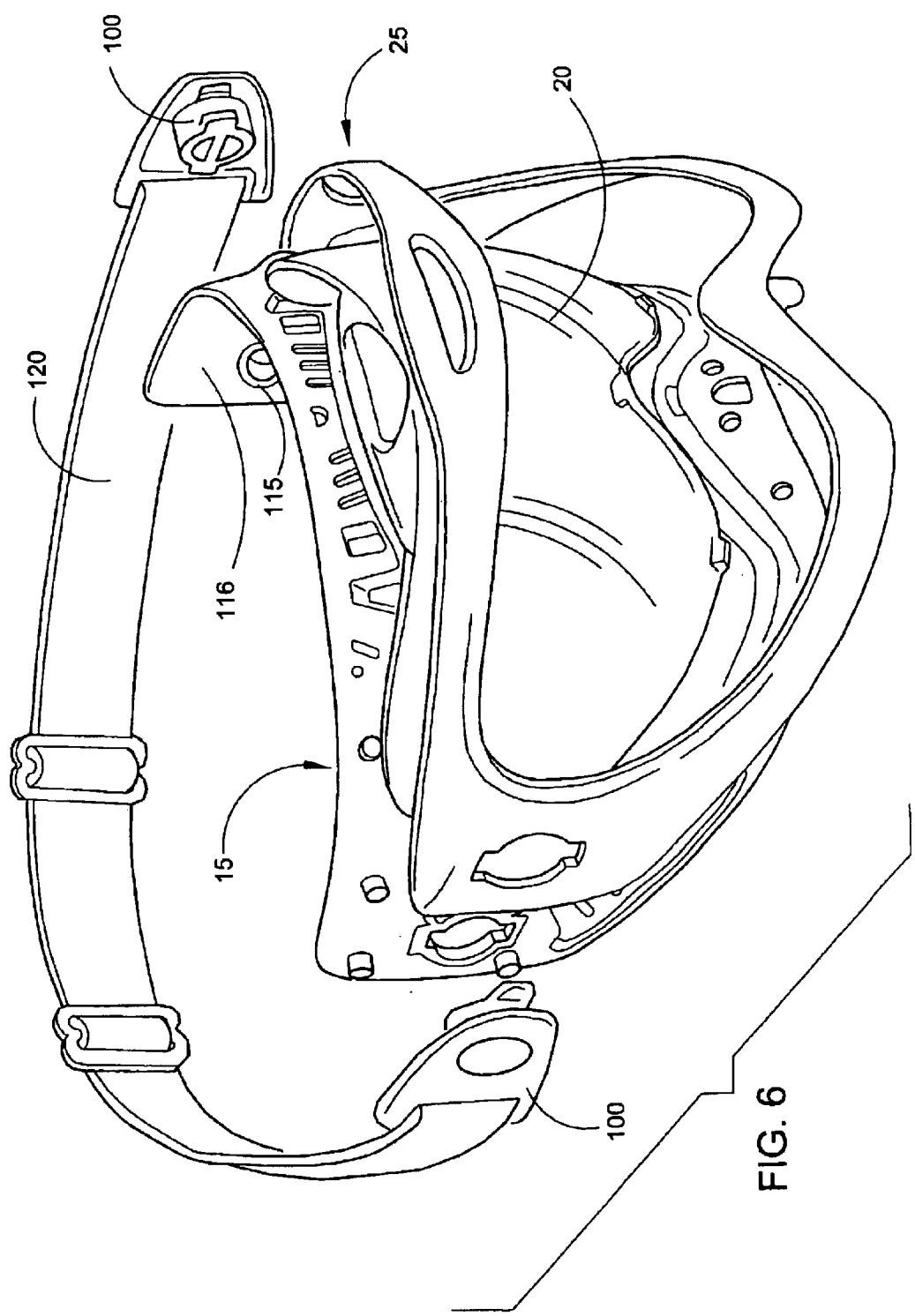
FIG. 6 is an exploded view of a lens assembly formed from a set of lens assembly parts including a lens.

When the set of lens-assembly parts is in operation, lens 20 is positioned or sandwiched between the base 15 and the frame 25 (FIG. 6). The lens 20 has a configuration which fits the lens receiving portion 30. The inner side 51 of the frame 25 is engaged with sections of the outer side 67 of the periphery 65 of the lens 20, namely, respective opposite brow 70, temple 75 and cheek 80, and nose 85 sections.

In a version of the set of lens-assembly parts, the opposite terminal regions 62 include fasteners 100. When releasably tightened or locked, the fasteners tension the lens receiving portion 30 of the base 15 and the inner surface 51 of the frame 25 against the inner and outer surfaces of the lens periphery 65, thereby fixing or clamping or otherwise securing lens 20 between the base 15 and the frame 25.

Figure 7:
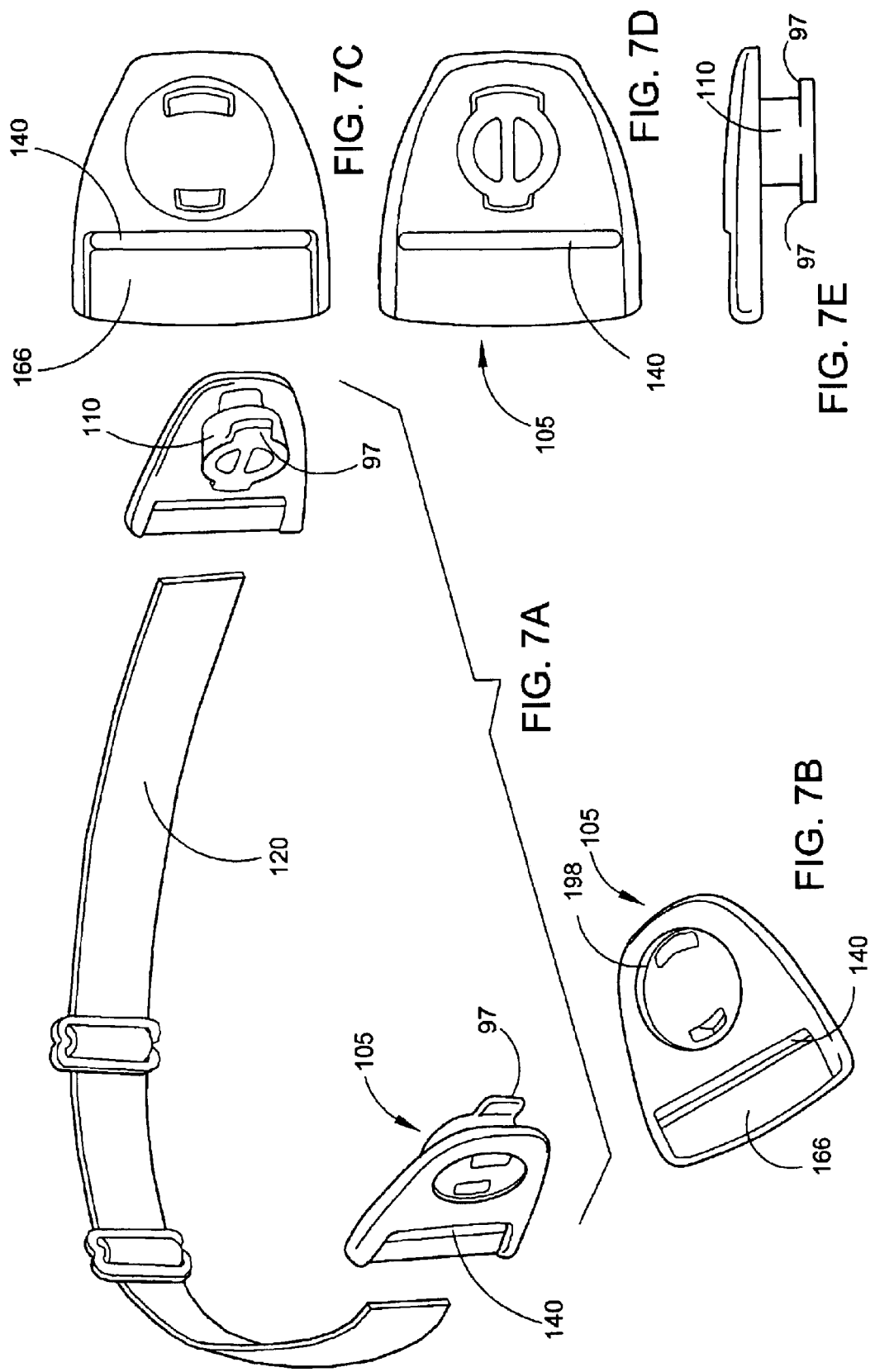
FIGS. 7A–7E shows an exploded assembly of a twist lock cam fastener with a strap, and various views of a twist lock cam fastener.

In one set of embodiments, the fastener 100 cooperates with registration openings 90 formed in the terminal section 45 and 60 of the frame and in the base. A coupler 105 extends into and about the registration openings 90 (FIG. 7A). Typically coupler 105 includes a protruding element 110 and a retention element that engages with registration openings 90. Examples of couplers include, but are not limited to, twist lock cams 97 (a cam inserted through registration opening 90 and fitting into a cam channel formed about the side of registration opening 90 that is situated on the inner side of base 15, (FIG. 6)). Other protruding elements 110 can be selected from bolts, rods, dowels, lugs, pins, rivets, and screws, while a retention element is selected for mating engagement with the protruding element. Retention elements are well known to those in the art, and include, without limitation, tightenable collars, annular members for frictional and/or snapping engagement with protrusion elements, and threaded openings. The fastener may also be formed in whole or in part from hook and loop materials positioned on or about the fastener in the terminal regions.

Preferred versions of the set of lens-assembly parts involve fasteners which the user can easily unfasten. Easy and quick unfastening results in easy, quick, and convenient disassembly of a lens assembly of the invention and removal of the lens 20 for cleaning or replacement, which is advantageous to the user. The base and frame can be easily cleaned and adjusted. In particular, quick and easy disassembly of the lens assembly allows the user to clean the peripheral portions of the lens 20, the lens receiving area of the base 15, and the inner surface 51 of the frame 25. These areas collect solid or liquid debris that tend to corrode, craze, crack or otherwise weaken a lens, frame or base, and which are difficult to access for cleaning in conventional lens assemblies. Additionally, quick and easy disassembly allows replacement of the frame 25 with frames of other shape, size, color, design or ornamental design provided that a replacement frame is structured for registration with the base unit as described herein.

When fastener 100 comprises a twist lock cam 97, slots of matching size to twist lock cam 97 are formed on surfaces of the frame 25 and base 15, the slots being in juxtaposition to define registration opening 90 and to secure lens 20 between the frame 25 and the base 15. Twist lock cams 97 and registration openings 90 are sized and positioned to correspondingly mate into sufficiently tight engagement (snapping engagement) to secure the lens, typically with a ¼ turn of protuding element 110, yet be subject to easy unsnapping by the user with a reverse ¼ turn. Fastener 100 and registration openings 90 may be positioned in the terminal region or in the regions or in the region of the base 15 and frame 25 which fit over the user's brow, cheeks, nose or any combination of those regions or sections of the base 15 and frame 25 so long as they arranged and sized for snapping engagement and easy unsnapping. Continuous or discrete areas of hook and loop fabrics can be positioned on surfaces of the frame 25 and base 15 which will be in juxtaposition for securing lens 20 between the frame 25 and the base 15. Interengagement of the hook and loop surfaces achieves securing of the lens 20 between the frame 25 and the base 15.

Another embodiment of the set of lens-assembly parts involves a fastener which is a clamp or sliding clip which fits about the terminal portions of the opposite temple portions of the base 15 and 25. A fastener takes the form of a flexible band which wraps about the opposite temple portions and tighteningly engages, securing the lens 20 between the base 15 and the frame 25. Hook and loop material disposed on a band provides surfaces on the band for interengagement and tightening. It is preferred to use a wrapping fastener that is easily untightened.

Another version of the set of lens assembly parts further comprises a strap 120 (FIGS. 5, 6, 7A, and 11) which is attached to couplers 105. The strap 120 is sized for the head of the user and fits the lens assembly to the head.

It is understood that fastening the frame 25 to the base 15, which sandwiches the lens 20 into a secure position, is achieved by one or a combination of the above-enumerated structures and devices, and that the invention is not limited to embodiments which do not comprise more than one of the above so enumerated structures and devices.

Figure 8:
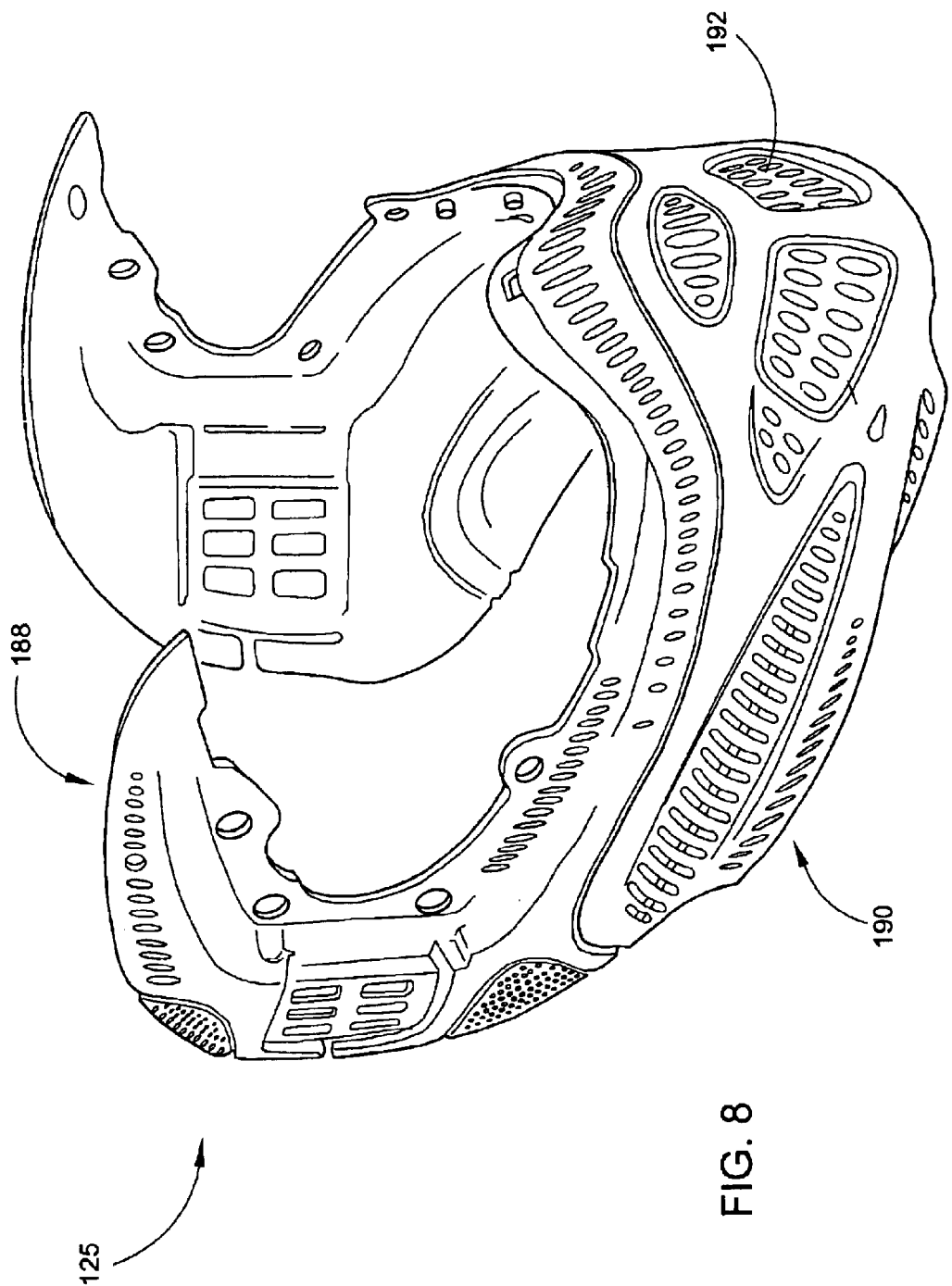
FIG. 8 is a perspective view of a mask.
Figure 9:
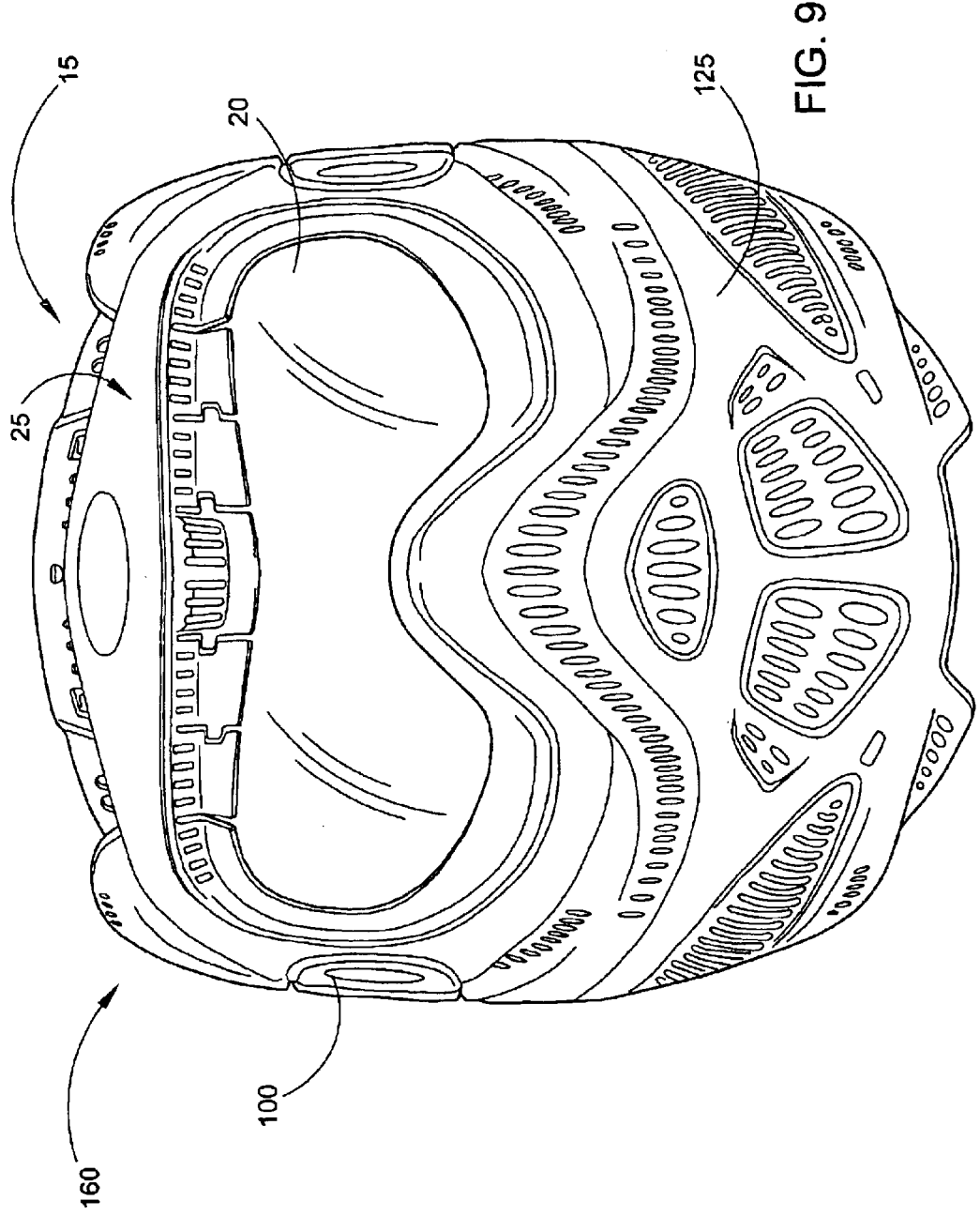
FIG. 9 is a front view of a lens assembly which includes a mask.
Figure 10:
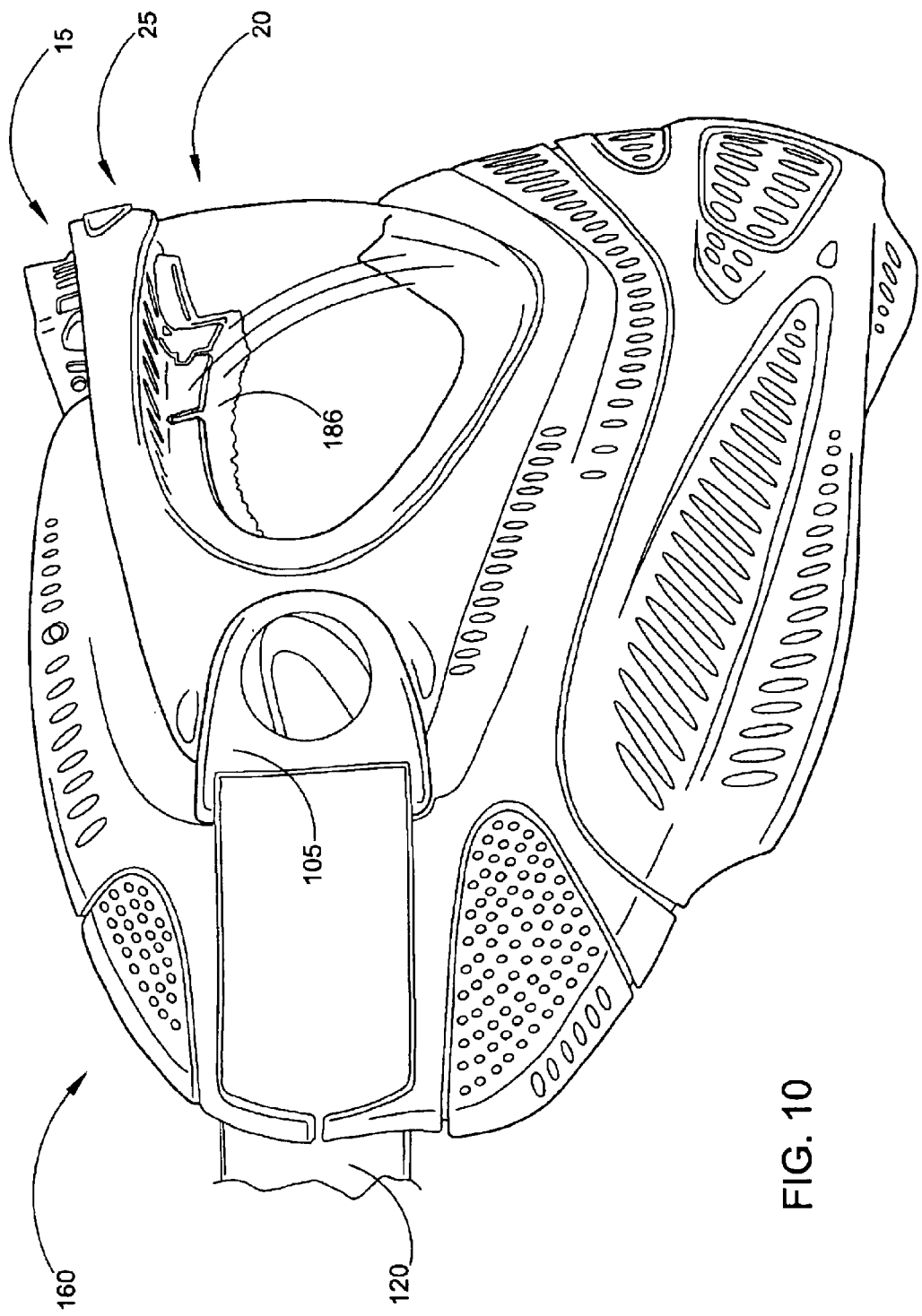
FIG. 10 is a side view of a lens assembly which includes a mask.
Figure 12:
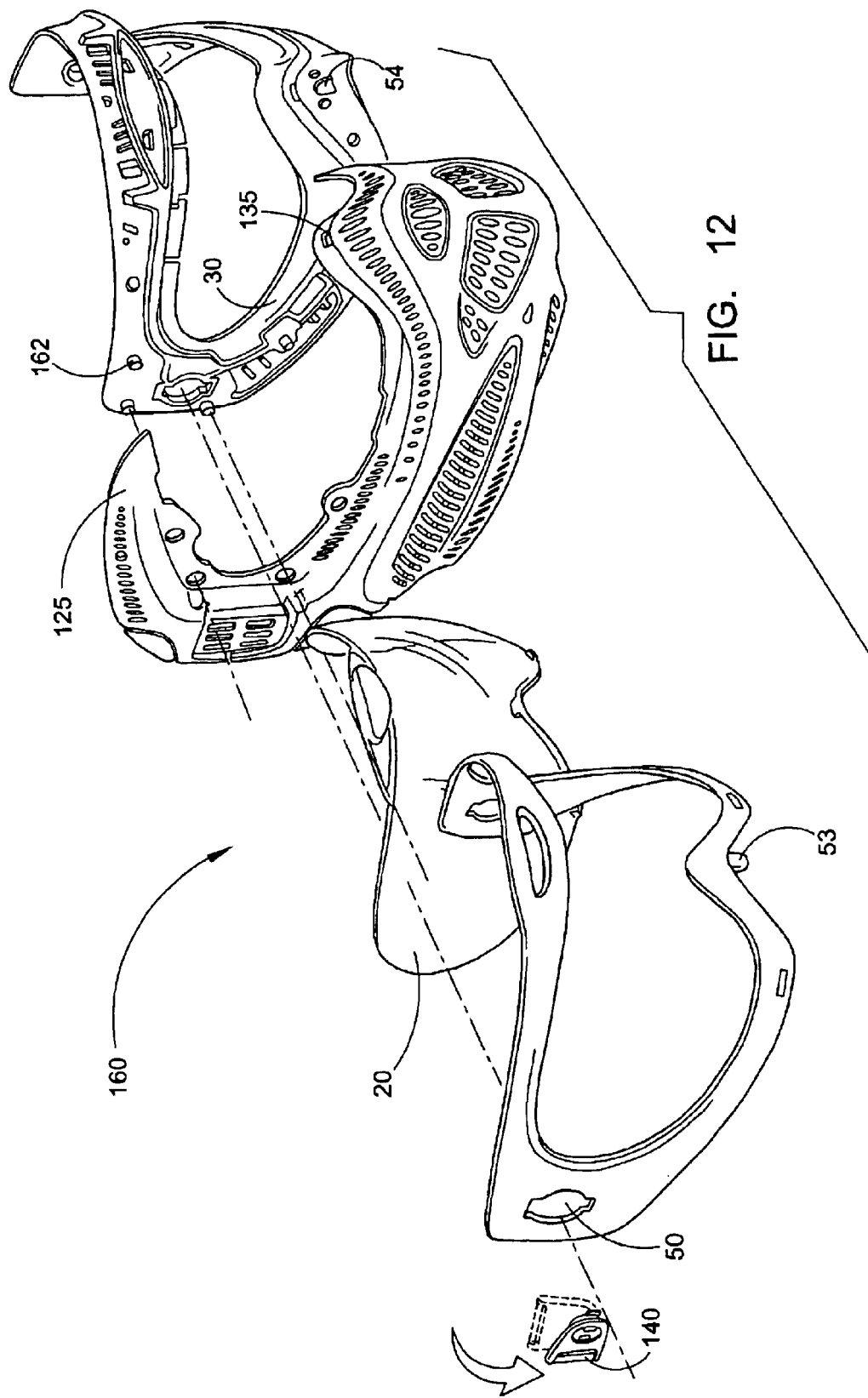
FIG. 12 is a second exploded view of a lens assembly including a mask.
Figure 13B:
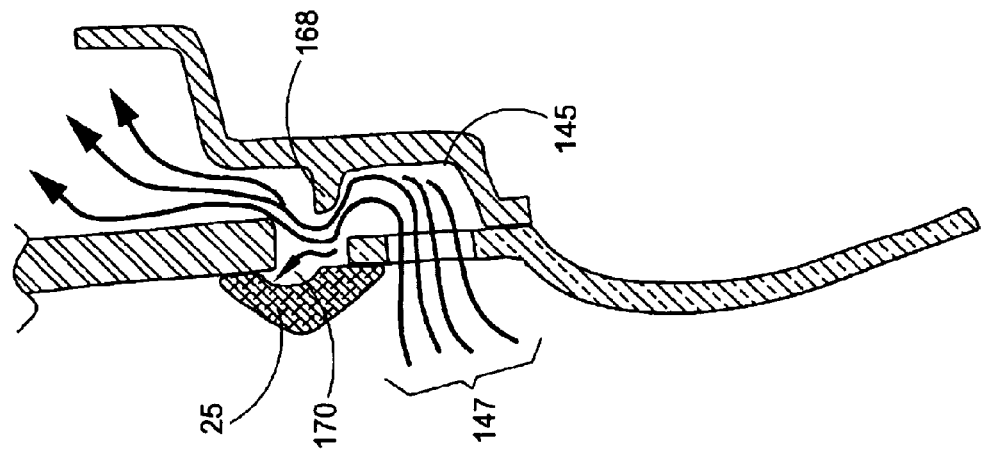
FIGS. 13A–13B shows holes in the mask and channels formed in the base to form a ventilation system and the related air flow.
Figure 13A:
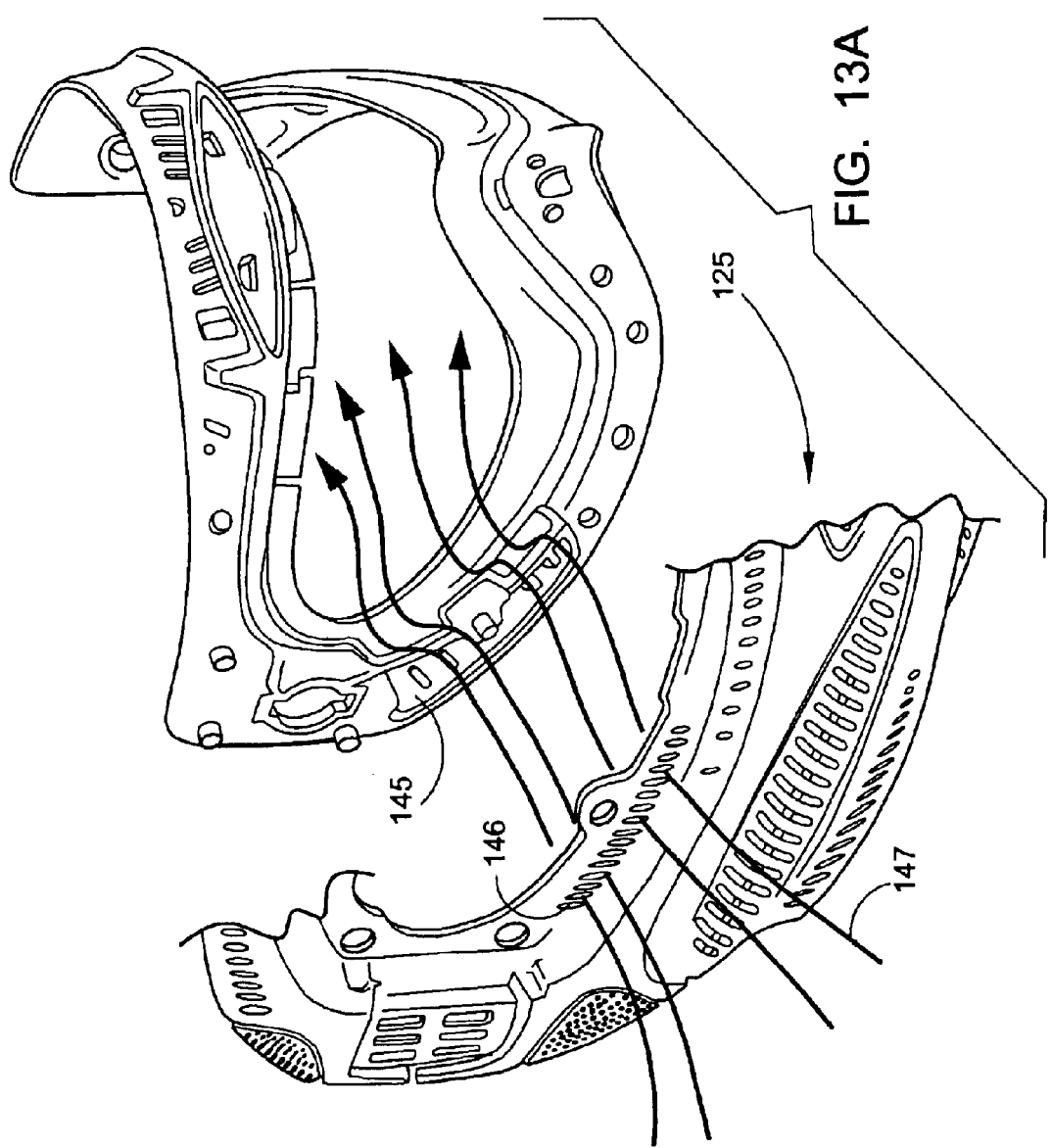
Figure 15B:
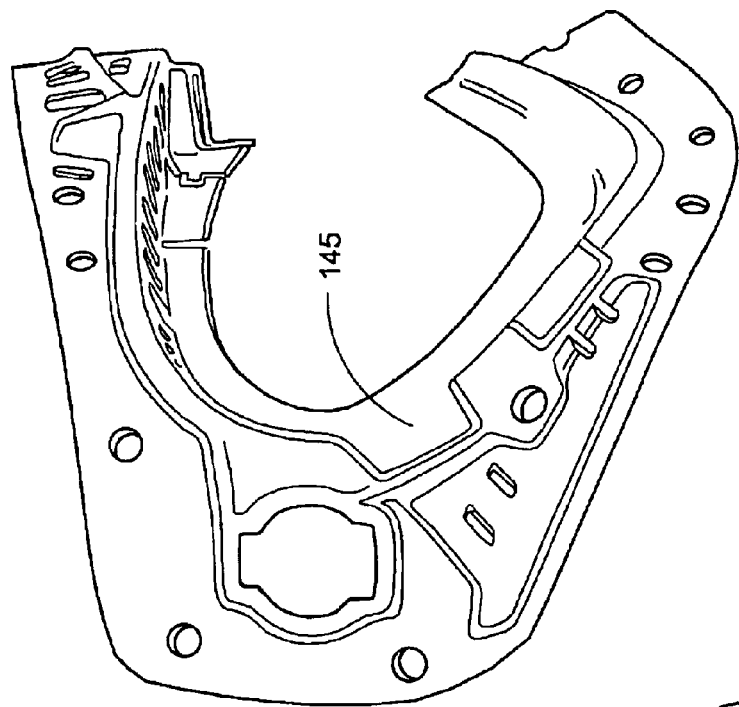
FIGS. 15A–15B show side views of the air flow pattern under the lens, and of the channels formed in the base.
Figure 15A:
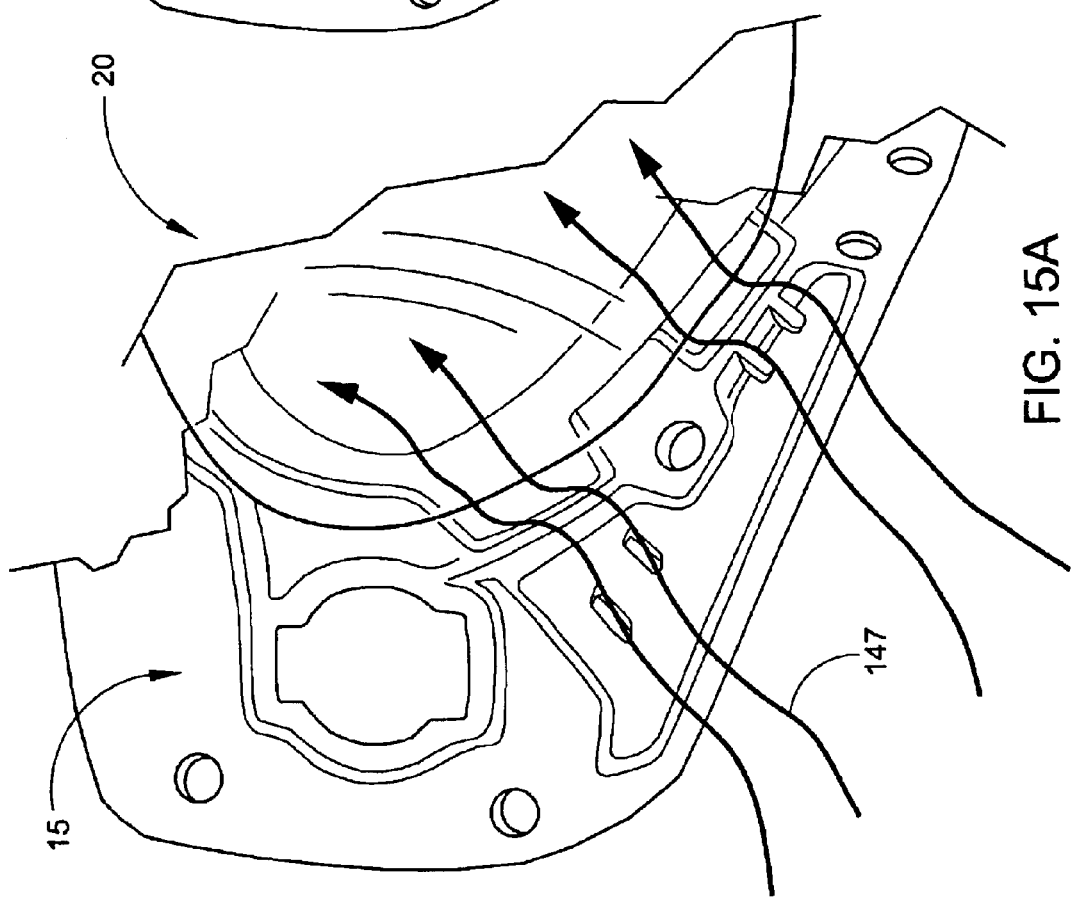

Another embodiment of the set of lens-assembly parts further comprises a mask 125 (FIG. 8) for engagement with the base 15, to provide for a mask system 160 (FIG. 12). The mask 125 is shaped or configured to cover at least a portion of the face. As shown in FIGS. 9 and 10, the mask section is configured to cover the user's nose, chin, lateral and temple regions of the forehead, and cheeks. The mask is formed from plastic which can have a durometer rating varying from soft to hard, depending on the requirements of the user for impact protection. A preferred version of the mask is formed from semi-soft plastic having two hardness levels, and which are co-molded as one piece. As shown in FIG. 8, the mask may comprise an upper portion 188 made of a semi-soft plastic material, and a lower portion 190 having different degree of softness. For instance, ventilation vanes 192 may be grouped in clusters and made of a plastic material softer than the remainder of lower portion 190.

Methods of molding plastics are well known in the art. One method of making a mask comprises the use of materials having more than one hardness and shaped by using a two-shot injection molding process, wherein both the harder and softer materials are sequentially injected in the same mold. Two-shot injection molding processes are known in the art, and thus will not be described in detail. During the hardening of the rigid plastic and rubbery materials in the two-shot molding process, a chemical bond is formed at the junction of the two materials, thereby permanently bonding the two materials together. This type of molding process provides for ease of manufacture, and further provides a long lasting construction. The manufacture of the set of lens-assembly part or lens assembly of the invention is not limited to the molding procedure described above.

Figure 4:
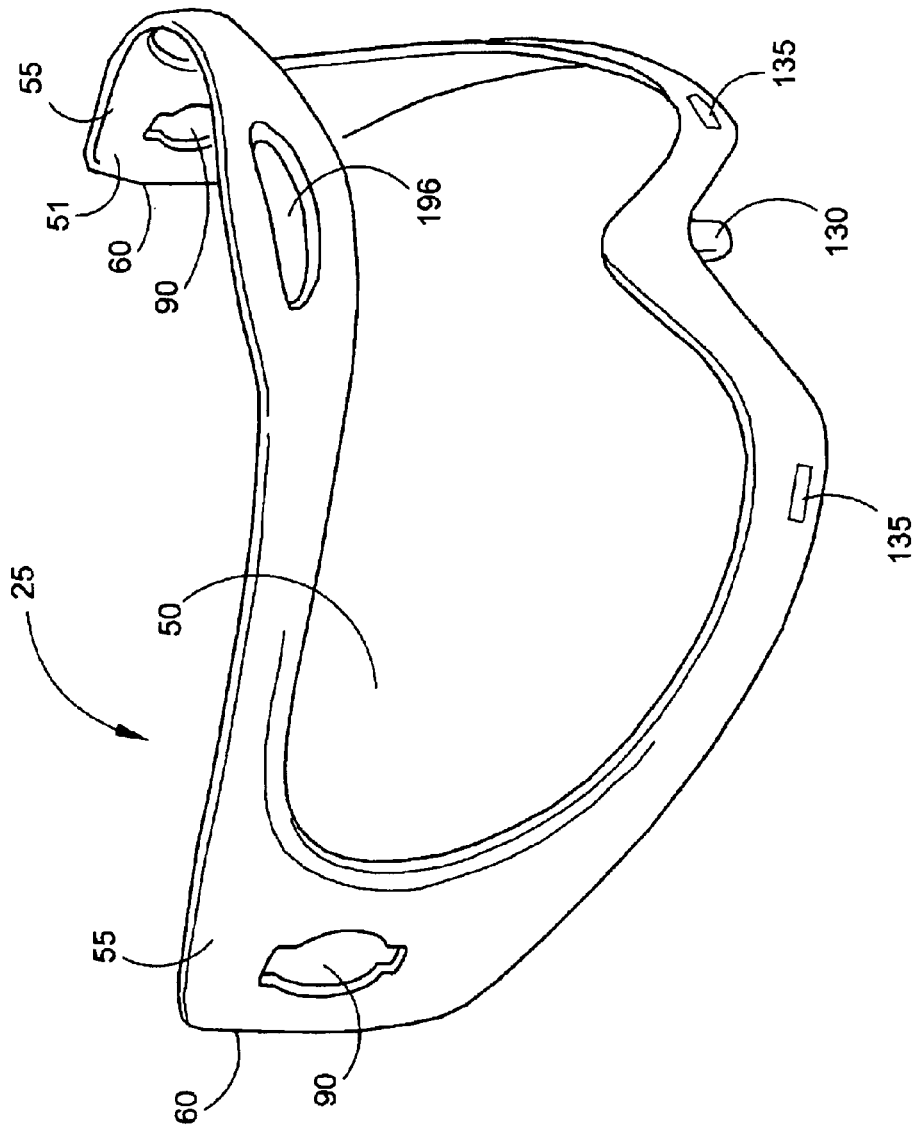
FIG. 4 is a perspective view of a frame.
Figure 5:
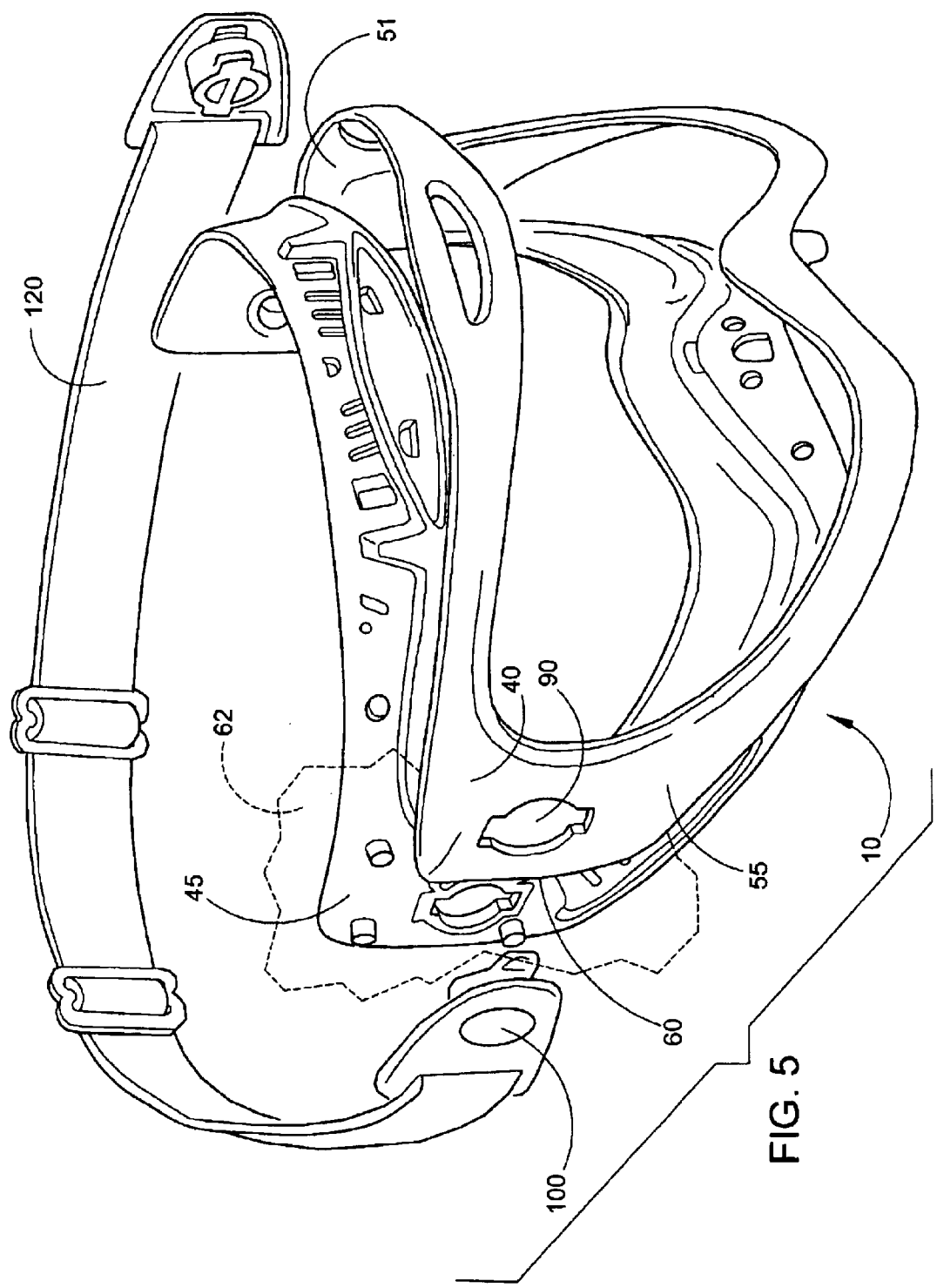
FIG. 5 is an exploded view of a lens assembly formed from a set of lens-assembly parts without a lens.
Figure 11:
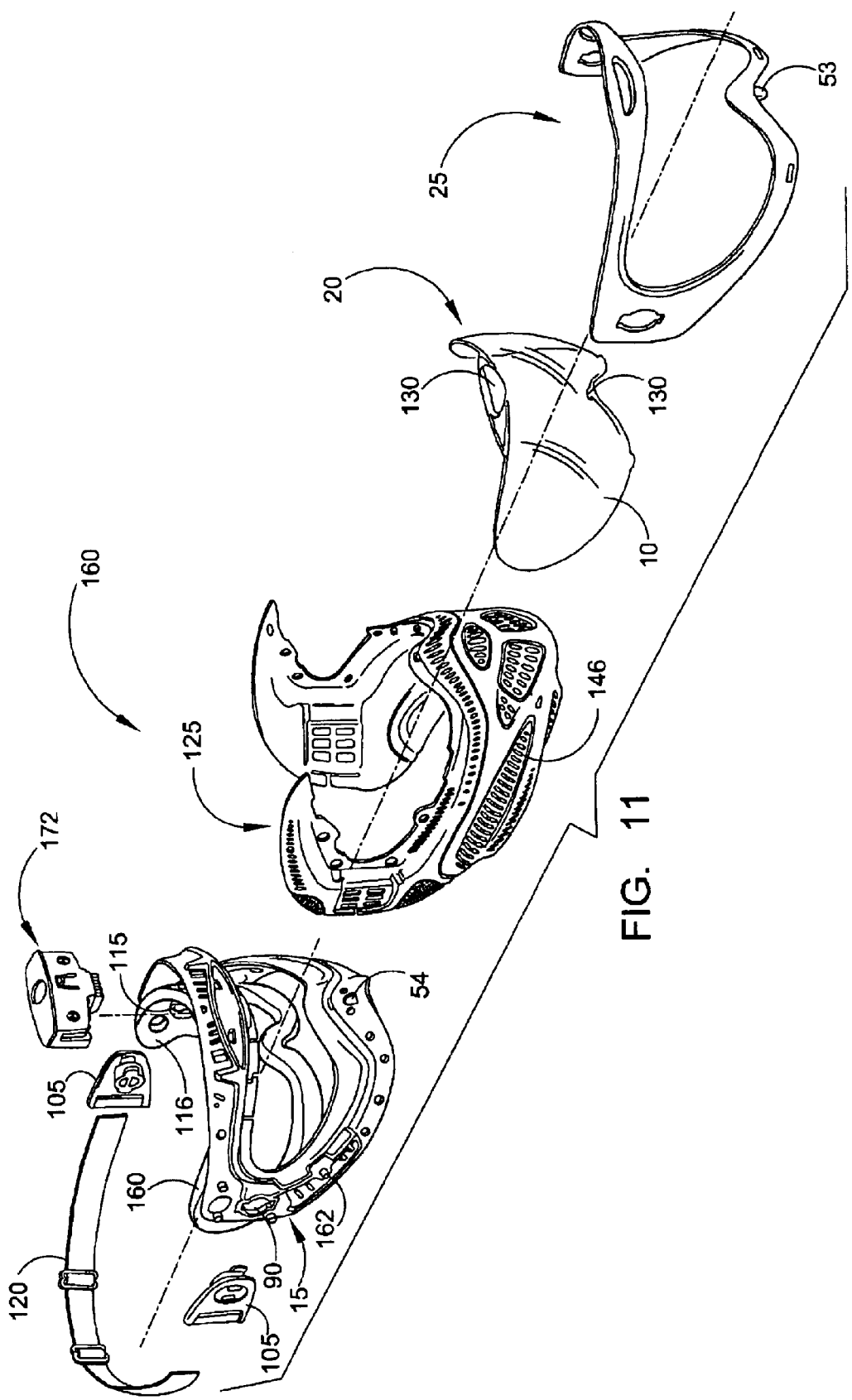
FIG. 11 is a first exploded view of a lens assembly including a mask and related elements.

The base 15, frame 25 and lens 20 are advantageously inter-engaged through a series of tabs 130 and slots 135 formed therein, and which are sized and positioned to correspondingly mate into engagement (FIGS. 1, 3, 4, 11 and 12). FIG. 1 discloses a base 15 which contains lens one or more lens retention slots 135. FIG. 4 illustrates a frame in which slots 135 are formed on the periphery. FIG. 3 illustrates a lens 20 in which tabs 130 are formed in the periphery. The tabs 130 and slots 135 of the base 15, lens 20, and frame 25 are positioned in registration so that, as shown in FIG. 11, tabs 130 of the lens 20 fit in registered slots of the base 15 and slots of the frame 25 (in the embodiment shown in FIG. 3. one nose tab extends rearwards and one tab in each cheek region extends forward). Further, a logo tab 194 extends to fit in logo slot 196, and may be visible to an outside observer (FIG. 3B) or hidden (FIG. 3C). Such a tab-slot combination prevents a vertical movement of lens 20, yet provides for an easy assembly and disassembly of lens 20 between base 15 and frame 25. such easy assembly and disassembly is further expedited by the use of fasteners 100 that can be locked in position with only a ¼ turn, as explained above.

FIGS. 6 and 11, which are exploded view of the lens assembly 160, illustrate registration openings 90 formed in opposite terminal sections of the frame 25 and the base 15. Inserted through each registration opening 90 is a coupler 105, such as a coupler comprising twist lock cam 97 (FIG. 7A). Lock cam 97 fits in a cam chamber 115 formed on the inner surface 116 of the base 15 and located about the registration opening 90. The lock cam 97 travels into the cam chamber 115; upon twisting lock cam 97 by a ¼ turn, lens 20 is secured in place between the frame 25 and the base 15. Merely twisting in another direction by a reverse ¼ turn unlocks lens 20, releasing the pressure which kept the lens 20 secured between the frame 25 and the base 15. Unfastening one or both fasteners 100 leads to rapid, easy disassembly of the lens assembly.

FIGS. 9, 10 and 11 illustrate a version of the invention in which the set of lens-assembly parts, and the mask system 160 formed therefrom, includes mask 125 attached to the base 15. Although FIG. 2 illustrates that the mask 125 is attached to the base 15 vis a vis a system of registered pins 162 and slots 164 (for instance, a total of twelve slots 164 along the upper and lower central portions of base 15, and a total of eight pins 162 along the sides of base 15), the attachment of the mask 125 to base 15 is not limited to the embodiment illustrated here. The mask 125 may be permanently attached to the base 15, for example without limitation, by adhesives, co-molding, staples, screws. Alternatively, the mask 125 may be clipped, latched or otherwise removably secured with the base 15.

FIG. 2 is a side view of a base 15 in which mask-attaching holes 164 and pins 162 are formed and located in registration with mating holes and pins formed in the mask 125 (FIG. 8). FIG. 11 illustrates assembly of mask system 160. The registration holes and pins of the base 15 and mask 125 are aligned and mated, thereby attaching the mask 125 to the base 15. The lens 20 and frame 25 are assembled by aligning and mating the registration tabs 130 of the lens 20 with slots 135 on base 15 and frame 25. The nose areas of the lens-frame assembly and the base-mask assembly are aligned. The nose pin 53 on the frame 25 is inserted through an aligned nose pin hole 54 on the base 15, which achieves placement of the lens 20 into the lens-receiving portion 30 of the base. The openings in the opposite terminal sections 45 and 60 are aligned providing registration openings 90 and a coupler 105 is inserted through the registration opening 90. The user twists twist lock cam 97 by ¼ turn, thereby locking the lens 20 between the base 15 and the frame 25.

FIG. 11 schematically shows the alignment of the frame 25, lens 20, mask 125, base 15, and coupler 105, as well as the strap 120. The strap 120 is attached to the coupler 105 (See FIGS. 7A–7E). A strap slot 140 formed in coupler 105 retains or attaches the strap 120 to the coupler 105, which when inserted and locked into the registration openings 90, achieving attachment of the strap 120 to the lens assembly. A strap depression 166, adjacent to strap slot 140, provides stability to strap 120. Further, a logo depression 198 provides a suitable area for positioning a promotional logo. In any case, strap receiving elements, such as slots, fingers, frames may be formed on the base, or on the frame; and/or clips or clipping mechanisms, hinged clipping mechanisms, buckles, rivets, screws, adhesives for attaching a strap to the lens assembly may be positioned in the terminal regions of the lens assembly, and are preferably integral with the fastener 100, or in some instances, the strap may be molded directly into a terminal region of the lens assembly.

As shown in FIGS. 13A–13B and 15A–15B, the base 15 is provided with a series of gutters or concavities which form channels 145 to provide ventilation to the user's face. Each of channels 145 may comprise one or more segments. In the version of the lens assembly which comprises a mask 125, the mask 125 is preferably provided with a series of holes 146 in a position corresponding to channels 145, so to provide air flow 147 over the user's face. The operation of channels 145 may be better understood with reference to FIG. 13B. A baffle 168 delimits one end of channel 145, Air flow 147 is free to enter hole 146, flow over baffle 168 and reach the user's face. Instead, liquid substances impacting mask 125 (for instance, paintball during paintball games) are prevented from reaching the user's face by baffle 168, which deviates the liquid substance 170 in the direction of frame 25. Air flow through the recessed areas of channel 145 and under lens 20.

FIGS. 11, 14, and 16A–16B depict a lens assembly in which a battery-powered fan 172 is mounted on the central brow or forehead of the base 15. Fan 172 comprises a housing 151, on which there are side slots 149, bottom slots 174, and a retention clip 150. On base 15 there are instead side retention tabs 147, in position matching side slots 149, and bottom retention tabs 176, in positions matching bottom slots 174. The side and bottom retention tabs 147 and 176 hold the fan housing 151 tight against the back of the forehead area. As the fan housing is slid down between the side tabs 147, the fan retention clip 150 contacts the top center edge of the base. While inserting the fan housing 151, the retention clip 150 flexes back and snaps into the retention hole 178 (FIG. 16C). Fan 172 is activated by an on/off button switch 180, which is situated inside a depression 182 on housing 151. A logo disk 184 may optionally be positioned over on/off button switch 180, logo disk 184 being in a position that is essentially flush with housing 151. Logo disk 184 serves the double function of providing an aesthetically pleasing finish to housing 151 (displaying a logo if desired), and also of serving as an on/off button switch within easy reach of the user.

The set of lens assembly parts may further include a layer of material 186, for instance, foam, for cushioning and/or absorbing sweat, the layer being mounted on the inner side of the base 15 (FIG. 10).

What is claimed is:

1. A set of lens-assembly parts comprising:
    (a) a base shaped to fit over the eyes, the base having a lens-receiving portion, one or more first slots situated around the periphery of the lens receiving portion, and opposite temple portions, each temple portion having a first opening;
    (b) a frame having an inner surface and an outer surface, the frame comprising one or more second slots and opposite temple portions, each of the temple portions having a second opening, the frame being shaped for registration with the base, wherein the first and second openings are in matching positions to jointly define a registration opening;
    (c) a lens shaped for positioning between the base and the frame, the lens having a plurality of tabs extending from the lens in direction substantially perpendicular to the outer and inner surfaces of the lens and cooperating with the first slots and second slots; and
    (d) one or more fasteners for tensioning the base against the frame, each of the fasteners engaging one registration opening.

2. The set of claim 1, further comprising a mask attached to the base, the mask being shaped for covering at least a portion of the face, the mask being secured to the base and comprising a plurality of ventilation vanes.

3. The set of claim 2, wherein one or more fasteners comprise couplers, each of the couplers comprising:
    (a) a cap positioned against one end of the registration opening formed in said frame and said base;
    (b) a retention element positioned against the opposite end of the registration opening, and (c) a protruding element extending through the registration opening and connecting the cap and the retention element.

4. The set of claim 3, further comprising a strap for attachment to each of said couplers.

5. The set of claim 3, wherein the retention element is a twist lock cam of elongated shape, wherein the registration opening has a matching elongated shape, and wherein the twist lock cam is secured in position by a one-quarter turn around the longitudinal axis of the protruding element.

6. The set of claim 5, wherein the twist lock cam is secured in position within a groove defined at the matching end of the registration opening.

7. The set of claim 3, wherein the cap comprises a depression suited for lodging a disk carrying a decorative design.

8. The set of claim 3, wherein the at least one of the couplers comprises a slot for attaching a strap, and a depression for lodging a portion of the strap.

9. The set of claim 2, wherein the mask is secured to the base by a plurality of pins extending from the base into matching opening in the mask, and by a plurality of pins extending from the mask into matching openings in the base.

10. The set of claim 2, wherein the ventilation vanes are grouped in clusters.

11. The set of claim 10, wherein the mask is of molded plastic, and wherein the ventilation clusters are molded from a plastic of different hardness than the remainder of the mask.

12. The set of claim 2, wherein the base comprises one or more ventilation channels, wherein some of the plurality of mask ventilation vanes are in matching positions to the ventilation channels, and wherein the ventilation channels comprise one or more baffles to deflect a liquid impacting the ventilation vanes away from the face of the user while enabling the passage of air from the ventilation vanes to the face of the user across the ventilation channels and under the lens.

13. The set of claim 1, wherein said one or more fasteners comprise hook and loop fabric.

14. A lens assembly formed from the set of lens-assembly parts of any of claims 1, 2, 3, 4 and 13.

15. The set of claim 1, wherein at least one of the second slots extends through the entire thickness of the frame, the at least one of the second slots enabling the corresponding lens tab to be visible on the outer surface of the frame and to display a decorative design situated on the corresponding lens tab.

16. The set of claim 1, wherein the frame comprises a pin extending from the nose area of the frame and mating with a corresponding opening in the base.

17. The set of claim 1, further comprising a battery-powered fan having a housing, the fan being secured to the base and activated by an on/off switch.

18. The set of claim 17, wherein the on/off switch is positioned within a depression in the housing, and wherein a button of matching size is positioned within the depression, the button enabling the activation of the on/off switch and being suitable for displaying a decorative design.

19. The set of claim 17, wherein the housing comprises a retention clip and one or more slots, wherein the retention clip flexes during the positioning of the fan on the housing and then engages with a matching opening on the base when the fan reaches its operative position, and wherein the one or more slots on the housing engage with matching retention tabs on the base when the fan reaches its operative position.

20. The set of claim 1, further comprising one or more foam layers attached substantially around the lens receiving portion of the base, the one or more foam layers being attached to the side of the base opposite to the lens.

21. A lens assembly formed from the set of lens-assembly parts of any of claims 5–20.

* * * * *